United States Patent [19]
Lilje

[11] Patent Number: 4,502,999
[45] Date of Patent: Mar. 5, 1985

[54] NUCLEOPHILIC SUBSTITUTION PROCESS

[75] Inventor: Kenneth C. Lilje, Baton Rouge, La.

[73] Assignee: Ethyl Corporation, Richmond, Va.

[21] Appl. No.: 487,038

[22] Filed: Apr. 21, 1983

[51] Int. Cl.³ .......................................... C07C 121/50
[52] U.S. Cl. ............................................... 260/465 G
[58] Field of Search ................................... 260/465 G

[56] References Cited

U.S. PATENT DOCUMENTS 4,370,278  1/1983  Stahly et al. .................... 260/465 E

OTHER PUBLICATIONS

Golinski et al., Tetrahedron Letters, vol. 37, pp. 3495–3498, (1978).
Makosza et al., J. Org. Chem., vol. 45, pp. 1534–1535, (1980).
Makosza, Int. Conf. Chem. Biotechnol. Biol. Act. Nat. Prod. (Proc.), vol. 2, pp. 480–490, (1981).

Primary Examiner—Delbert R. Phillips
Attorney, Agent, or Firm—Donald L. Johnson; John F. Sieberth; Patricia J. Hogan

[57] ABSTRACT

In a process for preparing a 2-(fluoronitrobenzene)acetonitrile by reacting a fluoronitrobenzene with an alpha,alpha-disubstituted acetonitrile in an inert solvent and in the presence of a base, a solvent having a dipole moment not higher than about 2.0 debyes is used to lead to the formation of a 2-(fluoro-2-nitrobenzene)acetonitrile. Preferred reactants are 2-fluoronitrobenzene and 2-chloropropionitrile, which lead to the formation of 2-(3-fluoro-2-nitrobenzene)propionitrile.

9 Claims, No Drawings

NUCLEOPHILIC SUBSTITUTION PROCESS

TECHNICAL FIELD

This invention relates to 2-(fluoronitrobenzene)acetonitriles and processes for preparing them.

BACKGROUND

As disclosed in U.S. Pat. No. 4,370,278 (Stahly et al.), it is known that 2-(fluoronitrobenzene)acetonitriles are useful for preparing flurbiprofen and related compounds and that the acetonitriles may be prepared by reacting a fluoronitrobenzene with an alpha-substituted alkyl cyanide in a substantially anhydrous aprotic solvent and in the presence of a base. Stahly et al. also teach that their reaction tends to be highly selective on the para positions of their fluoronitrobenzenes, and their Examples illustrate that selectivity.

There are pharmaceuticals and other materials which it is logical to believe could be formed from 2-(fluoronitrobenzene)acetonitriles having the acetonitrile substituent in a position ortho to the nitro substituent. It would therefore be desirable to find a way of modifying the Stahly et al. processes so as to make it possible to prepare such compounds.

Copending application Ser. No. 487,039, filed Apr. 21, 1983 in the name of Kenneth C. Lilje, discloses one such modification, the use of temperatures not higher than about 15° C.

SUMMARY OF INVENTION

An object of this invention is to provide novel processes for preparing 2-(fluoronitrobenzene)acetonitriles.

Another object is to provide such processes which lead to the formation of 2-(fluoro-2-nitrobenzene)acetonitriles.

These and other objects are attained by using a solvent having a dipole moment not higher than about 2.0 debyes in a process for preparing a 2-(fluoronitrobenzene)acetonitrile by reacting a fluoronitrobenzene with an alpha,alpha-disubstituted acetonitrile in an inert solvent and in the presence of a base.

DETAILED DESCRIPTION

Fluoronitrobenzenes utilizable in the practice of the invention include the 2-, 3-, and 4-fluoronitrobenzenes. As a rule, 2-fluoronitrobenzene is preferred, although the fluoronitrobenzene that might be preferred in any given instance generally depends on the derivative that is desired as the ultimate product.

The alpha,alpha-disubstituted acetonitriles that can be used in the practice of the invention include a variety of such compounds, which—in general—may be represented by the formula:

wherein L is a leaving group and R is a hydrocarbyl (e.g., alkyl, alkenyl, alkynyl, cycloalkyl, cycloalkenyl, aryl, aralkyl, etc.) or hydrocarbyloxyhydrocarbyl (e.g., alkoxyalkyl, aryloxyalkyl, alkoxyaryl, alkoxycycloalkyl, etc.) group which most preferably contains up to about 10 carbons.

Exemplary leaving groups, L, include halo, aryloxy, haloaryloxy, alkylthio, cycloalkylthio, arylthio, aralkylthio, haloalkylthio, halocycloalkylthio, haloarylthio, haloaralkylthio, or, less preferably, alkoxy, cycloalkoxy, aralkoxy, haloalkoxy, halocycloalkoxy, haloaralkoxy, and the like, as well as other suitable leaving groups which have been described in the literature, e.g., in Golinski et al., "'Vicarious' Nucleophilic Substitution of Hydrogen in Aromatic Nitro Compounds, *Tetrahedron Letters*, Vol. 37, pp. 3495-8 (1978); Makosza et al., "Vicarious Substitution of Hydrogen in Aromatic Nitro Compounds with Acetonitrile Derivatives," *Journal of Organic Chemistry*, Vol. 45, pp. 1534-5 (1980); and Makosza, "Some New Reactions of Carbanions. Vicarious Nucleophilic Substitution of Hydrogen in Nitroarenes," *Int. Conf. Chem. Biotechnol. Biol. Act. Nat. Prod.* (Proc.), 1st, 1982, issue 2, pp. 480–490.

When the leaving group is an organic group, it is generally preferred that it contain not more than about 10 carbons, although organic leaving groups having an even higher carbon content are satisfactory in the practice of the invention. Preferably, the leaving group is halo, i.e., chloro, bromo, fluoro, or iodo; and it is more preferably chloro or bromo, most preferably chloro.

A few examples of alpha,alpha-disubstituted acetonitriles that can be used in the practice of the invention are 2-chloropropionitrile, 2-chlorobutyronitrile, 2-chlorovaleronitrile, 2-chlorocapronitrile, 2-chloro-4-pentenenitrile, 2-chloro-3,3-dimethylbutyronitrile, 2-chloro-2-phenylacetonitrile, 2-chloro-2-cyclohexylacetonitrile, 2-chloro-3-(3-chloro-o-tolyl)propionitrile, 2-chloro-3-phenylpropionitrile, the corresponding bromo and iodo compounds, and the like. The alpha-halopropionitriles, i.e., alpha-haloalkyl cyanides containing at least three carbons—particularly 2-chloropropionitrile and 2-bromopropionitrile—are especially preferred, although similar cyanides in which the alpha-halo substituent is replaced by one of the other leaving groups mentioned above are also highly desirable.

The solvent used in a fluoronitrobenzene/nitrile reaction of the invention may be any solvent which is inert under the conditions of the reaction, i.e., any solvent that will not prevent the reaction from occurring, and which has a dipole moment not higher than about 2.0 debyes. Such solvents are substantially anhydrous and are generally aprotic, although solvents such as liquid ammonia are also utilizable.

Illustrative of the solvents which may be employed in the process of the invention are ethers such as diethyl ether, dibutyl ether, 1-ethoxyhexane, tetrahydrofuran, 1,4-dioxane, 1,3-dioxolane, diglyme, 1,2-diethoxyethane, anisole, etc.; tertiary amines such as pyridine, N-ethylpiperidine, triethyl amine, tributyl amine, N,N-diphenyl-N-methyl amine, N,N-dimethylaniline, etc.; and the like. Tetrahydrofuran is particularly preferred.

Bases useful in the practice of the invention include all bases strong enough to activate the nitrile reactant, e.g., alkaline earth metal compounds such as calcium oxide, calcium hydride, calcium hydroxide, barium oxide, barium hydroxide, magnesium hydroxide, zinc hydroxide, etc. However, the base is preferably an alkali metal compound, e.g., an organoalkali metal compound, alkali metal hydride, alkali metal hydroxide, alkali metal oxide, alkali metal amide, or alkali metal alcoholate, such as butyllithium, phenyllithium, ethylsodium, amylsodium, butylpotassium, benzylpotassium, sodium dimsylate (i.e., the sodium salt of diethylsulfoxide), sodium hydride, potassium hydride, sodium hydroxide, potassium hydroxide, sodium oxide, potassium oxide, sodium amide, potassium amide, lithium diisopropylamide, sodium methoxide, potassium t-butoxide, the sodium salt of the monomethylether of ethylene glycol, sodium phenoxide, and the like. Ordinarily the use of an alkali metal hydroxide or alkoxide, such as sodium hydroxide, sodium t-butoxide, or potassium t-butoxide will be found most preferable.

Use of an alkali metal compound as the base permits the alternatives of using the alkali metal compound alone or in conjunction with a phase transfer catalyst, such as a quaternary ammonium salt, ethylene glycol, or a suitable crown ether. When a phase transfer catalyst is employed (1) the alkali metal compound may be any of the alkali metal compounds generically or specifically indicated above, although the type of alkali metal compound being used determines the type of crown ether that is preferably utilized—lithium bases generally calling for the use of a 12-crown-4 ether, sodium bases generally calling for the use of a 15-crown-5 ether, and potassium bases generally calling for the use of an 18-crown-6 ether, and (2) the reaction medium may be any of the aprotic solvents mentioned above, or it may be an inert liquid hydrocarbon such as benzene, toluene, xylene, hexane, heptane, isooctane, or the like.

When an alkali metal hydride, especially a highly pure alkali metal hydride, is employed as the base, it is desirable to include a small amount of a transfer agent such as water, alcohol, or the like in the system. It is believed that the transfer agent activates the hydride by reacting therewith to form a small amount of the alkali metal hydroxide or alcoholate.

The process of the invention may be conducted at ambient temperatures, elevated temperatures, or—preferably—at temperatures not higher than about 15° C. to lead to the formation of 2-(fluoro-2-nitrobenzene)acetonitriles—the amount of orthoisomer, i.e., 2-(fluoro-2-nitrobenzene)acetonitrile, formed in a given solvent generally increasing with a decrease in the temperature employed. There is no lower limit on the temperature that may be used other than the practical one, i.e., the freezing temperature of the solvent being utilized. Generally the temperature is in the range of about −20° to about 15°, preferably about −15° to about 5°, most preferably about −10° to about 0° C., as in the aforementioned Lilje application, although it is an advantage of the present invention that such low temperatures do not have to be employed to permit the formation of 2-(fluoro-2-nitrobenzene)acetonitriles.

As in the process of Stahly et al., the fluoronitrobenzeneacetonitrile synthesis of the invention appears to occur by a nucleophilic substitution mechanism whereby the nitrile undergoes a nucleophilic substitution on an unsubstituted ring carbon of the fluoronitrobenzene during which an alpha-substituent of the acetonitrile functions as a leaving group. It is conducted in a substantially anhydrous reaction system, and accordingly, except when a small amount of water (which is itself consumed by reaction with the alkali metal hydride) is employed as a transfer agent, the components of the reaction system should be brought together and maintained under a dry inert atmosphere. Thus, while it is possible to conduct the process in the presence of air, it is desirable to maintain the reaction system under an atmosphere of dry nitrogen or the like.

The fluoronitrobenzene and alpha,alpha-disubstituted acetonitrile may be used in amounts such as to provide a stoichiometric excess of either of the reactants or the stoichiometric amount of each. However, when a stoichiometric excess of the fluoronitrobenzene is employed, the quantity of product obtainable will be limited by the quantity of nitrile used, so it is desirable to utilize a stoichiometric excess of the nitrile. The amount of base employed is preferably such as to provide at least two molar equivalents of base per mole of fluoronitrobenzene, since the use of smaller amounts—although permitting the reaction to occur—makes the base the limiting reagent.

The mode of addition of the ingredients of the reaction system is not particularly critical. Accordingly, it is convenient to add the fluoronitrobenzene to a mixture of the other materials, add the base to a mixture of the other materials, add the reactants to a mixture of the base and inert solvent, introduce all four ingredients simultaneously into the reaction zone, or the like. Since the reaction ordinarily proceeds very rapidly, long reaction times are not required. The reaction will usually be completed within a matter of minutes or a few hours at the temperatures of the reaction.

When derivatives of the fluoronitrobenzeneacetonitriles are desired, they may be prepared by employing conventional techniques to convert to the desired derivatives the fluoronitrobenzeneacetonitriles made in accordance with the present invention.

As indicated above, the present invention is particularly advantageous in providing a readier and more economical route to the synthesis of pharmaceuticals and other chemical products that can be prepared from 2-(fluoro-2-nitrobenzene)acetonitriles, most notably products such as compounds disclosed in U.S. Pat. Nos. 3,600,437, 4,126,635, and 4,182,774.

The following examples are given to illustrate the invention and are not intended as a limitation thereof.

EXAMPLE I

A suitable reaction vessel was charged with 17 ml of tetrahydrofuran (THF) and cooled to −5° C. under nitrogen. Then 42.5 mmols of potassium t-butoxide were added, followed by a mixture of 22.3 mmols of 2-chloropropionitrile and 17.7 mmols of 2-fluoronitrobenzene in 3 ml of THF. The addition took 10 minutes, during which the temperature was maintained between 0° and −10° C. After the addition, the reaction mixture was stirred for 40 minutes at a temperature below 0° C., quenched, and worked up. The process resulted in the production of 3.7 g of a red-brown oil, which vpc analysis showed to contain 10 area % of 2-(3-fluoro-4-nitrobenzene)propionitrile and 20 area % of 2-(3-fluoro-2-nitrobenzene)propionitrile.

EXAMPLE II

Following the same general procedure as in the previous example, 8.9 mmols of 2-fluoronitrobenzene were reacted with 12.2 mmols of 2-chloropropionitrile in 15 ml of THF and in the presence of 61.3 mmols of sodium hydroxide. However, the reaction was conducted at 30° C., and stirring at the reaction temperature was continued for three hours after addition of the reactants had been completed. Analysis of the product showed the significant product to be 2-(3-fluoro-2-nitrobenzene)propionitrile.

It is obvious that many variations may be made in the products and processes set forth above without departing from the spirit and scope of this invention.

I claim:

1. In a process for preparing a 2-(fluoronitrobenzene)acetonitrile by reacting a fluoronitrobenzene with an alpha,alpha-disubstituted acetonitrile in an inert solvent and in the presence of a base, the improvement which comprises conducting the reaction in a solvent having a dipole moment not higher than about 2.0 debyes so as to form a 2-(fluoro-2-nitrobenzene)acetonitrile.

2. The process of claim 1 wherein the fluoronitrobenzene is 2-fluoronitrobenzene.

3. The process of claim 1 wherein the alpha,alpha-disubstituted acetonitrile is an alpha-haloalkyl cyanide containing at least three carbons.

4. The process of claim 3 wherein the alpha,alpha-disubstituted acetonitrile is alpha-chloropropionitrile.

5. The process of claim 1 wherein the solvent is tetrahydrofuran.

6. The process of claim 1 wherein the base is an alkali metal compound.

7. The process of claim 6 wherein the base is an alkali metal hydroxide.

8. The process of claim 6 wherein the base is an alkali metal alkoxide.

9. The process of claim 1 wherein the fluoronitrobenzene is 2-fluoronitrobenzene, the alpha,alpha-disubstituted acetonitrile is alpha-chloropropionitrile, the inert solvent is tetrahydrofuran, and the base is an alkali metal hydroxide or alkoxide.

* * * * *